Figure 1:
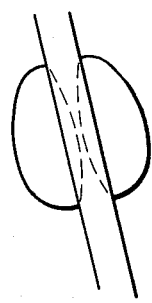

United States Patent [19]
Northeved

[11] 3,942,530
[45] Mar. 9, 1976

[54] PROSTATE RESECTOSCOPE HAVING ULTRASONIC SCANNING

[75] Inventor: Allan Northeved, Bagsvaerd, Denmark

[73] Assignee: Akademiet for de Tekniske Videnskaber, Svejsecentralen, Glostrup, Denmark

[22] Filed: Sept. 4, 1974

[21] Appl. No.: 503,191

[30] Foreign Application Priority Data
Sept. 3, 1973  Denmark.......................... 4839/73

[52] U.S. Cl................................ 128/303.15; 128/4
[51] Int. Cl.²......................................... A61B 17/32
[58] Field of Search..... 128/303.15, 303.13, 303.14, 128/303.17, 4-9, 2 V, 2.052, 24 A

[56] References Cited
UNITED STATES PATENTS

| | | |
|---|---|---|
| 2,764,149 | 9/1956 | Sheldon.................................. 128/6 |
| 2,888,017 | 5/1959 | Wallace........................... 128/303.15 |
| 3,149,633 | 9/1964 | Zingale........................... 128/303.15 |
| 3,532,037 | 10/1970 | Nevilly...................................... 128/6 |
| 3,779,234 | 12/1973 | Eggleton et al...................... 128/2 V |
| 3,827,115 | 8/1974 | Bom................................. 128/2.052 |

*Primary Examiner*—Robert W. Michell
*Assistant Examiner*—Lee S. Cohen
*Attorney, Agent, or Firm*—Ladas, Parry, Von Gehr, Goldsmith & Deschamps

[57] ABSTRACT

The conventional fibre optics in a cystoscope is replaced by a scanning device by which it is possible to obtain an ultrasonic scanning picture of the interior of a human body, especially the bladder and the prostate region. Essentially, the scanning device comprises an elongated tube mounted on a stepping motor. From the distal end of this tube a cautery electrode protrudes, the distal end further being provided with a transducer for pulse-echo ultrasonic exploration.

1 Claim, 5 Drawing Figures

U.S. Patent   March 9, 1976   3,942,530

PROSTATE RESECTOSCOPE HAVING ULTRASONIC SCANNING

The invention relates to a prostate resectoscope of the type comprising a long, hollow, thin tube through which are carried a pair of mutually electrically insulated wires, which at the distal open end of the tube are stripped and joined together so as to form a cautery electrode.

Elderly people often suffer from prostatic hypertrophy, which may cause dysuria. This disease is cured by means of a prostate resectoscope, by means of which the urethral glandular tissue forming the stricture is cauterized and curetted by means of the cautery electrode and rinsed away.

In order that the person performing the operation might be able to orient himself fibre optical means have been used, which make it possible to illuminate the interior of the prostate and thus to watch the progress of the operation. Such an instrument functions satisfactorily as long as the form of the prostate is normal, i.e. that the wall of the prostate is of even thickness round the urethra, so that there is no risk of cauterizing/scraping (resecting) too much tissue away and thereby of going through the wall and causing an undesired haemorrhage. However, this is not always the case. Often the prostate is partially very thinwalled, and such cases cannot be ascertained by the optical means hitherto used.

The present invention provides a prostate resectoscope of the type stated in the opening paragraph, said resectoscope comprising a first elongated hollow cystoscope tube surrounding a second elongated tube of a material inert to body tissues and fluids, said second tube being mounted on the output shaft of a stepping motor to rotate said second tube within said first tube, said first tube further having fixedly mounted therein a pair of electrically insulated conductors, which at the distal end of said first tube and said second tube are stripped and joined together to provide a cautery electrode protruding from said distal end, said second tube further comprising fixedly mounted therein at said distal end an ultrasonic transducer to transmit a beam of sound energy and to receive reflected sound energy from tissue interfaces in the prostate region to obtain as the second tube is rotated within the first tube an ultrasonic scanning picture in B-representation of a section of the prostate region to indicate where to make a resection in said section of the prostate region.

By replacing the optics of a resectoscope by such a scanning device, which can be rotated by means of the stepping motor, it is rendered possible to provide an ultrasonic scanning picture (in sectional view) on the screen of an oscilloscope. Hereby is obtained clear visual information of where the resection ought absolutely not to be made, and where the resection involves no risk.

Further, the scanning device is constructed so as to be fully interchangeable with the optics so that a very useful aid in connection with cystoscopy is thus provided.

Figure 2:
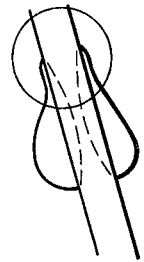
Figure 3:
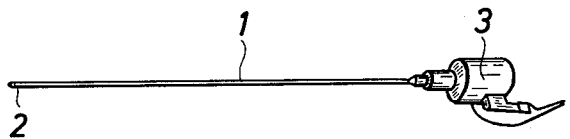
Figure 4:
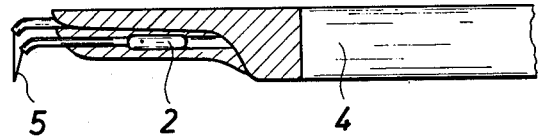
Figure 5:
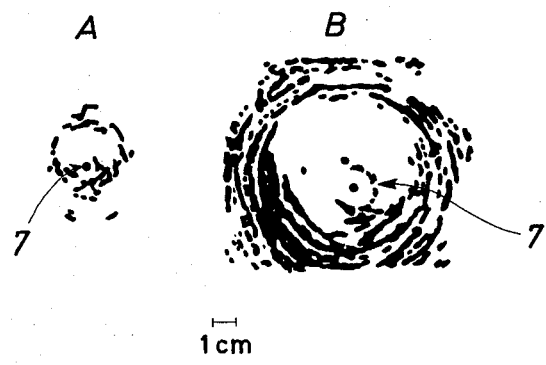

The invention will be described below with reference to the accompanying drawings, in which:

FIG. 1 is a diagrammatic sectional view of a stricture (dotted line) of a urethra with an evenly thickwalled prostate, FIG. 2 is a diagrammatic sectional view of a urethra having a partially very thin-walled prostate, FIG. 3 is a scanning device according to the invention, FIG. 4 is the tip of the scanning device on an enlarged scale and introduced into a resectoscope, and FIG. 5 is an ultrasonic scanning picture of the prostate taken while a prostate resectoscope according to the invention was being used.

FIG. 1 shows a case of prostatic hypertrophy which will not cause any problems in connection with the resection, whereas FIG. 2 shows a case, in which a resection involves a serious risk of going through the prostate and thereby of causing a haemorrhage. The critical area of the prostate is marked by a circle.

The scanning device is shown in FIG. 3 and as already mentioned, it is constructed to be fitted into a cystoscope instead of the optics belonging thereto. It comprises an elongated tube 1 of stainless steel or another material which is inert to body tissues and fluids. At the very end of this tube an ultrasonic transducer 2 is mounted, whereas at the other end a stepping motor 3 is mounted, which is controlled by a control unit, which is not shown. The transducer is made of barium titanate and placed parallel with the longitudinal axis of the tube and has a direction of emission which is identical with the radius going through its centre. To prevent accidents the front of the transducer is connected to earth (the stainless tube), whereas the other terminal is led centrally through the tube 1. FIG. 4 shows the ultrasonic transducer 2 placed in a resectoscope 4. Furthermore, the cautery electrode 5 is shown. A detailed description of such a resectoscope is not given as the construction of such an instrument is well-known to those skilled in the art.

The resectoscope 4 being fixedly mounted it is thus possible to rotate the ultrasonic transducer 2 by means of the stepping motor 3 so that the scanning device rotates on its longitudinal axis like a radar antenna.

Thus the scanning method employed is a combination of the impluse-echo-system used in an ultrasonic system and the way of visualization normally used in a radar system. Thus, every second a large number of mechanical pressure waves of very short duration are emitted from the transducer, in which electrical impulses are converted into mechanical impulses and vice versa. After the emission of each individual pressure wave a sensitive receiver is switched on. The mechanical impulses being reflected from tissue interfaces are again converted into weak electrical voltages in the transducer, said voltages after amplification being visualized on the screen of an oscilloscope. Thus, the same transducer is here used both as an emitter and as a receiver. The rotational centre of the transducer is displayed as a bright spot in the centre of the oscilloscope screen. The echo information is visualized on the screen by way of small light dots appearing on a radius rotating synchronously with the transducer. The screen of the oscilloscope is to have a reasonably short afterglow which will ensure that the picture is renewed for each revolution of the transducer.

FIG. 5 shows an example of an ultrasonic scanning picture very much like a normal radar picture. The scanning picture A represents a prostate of normal size, whereas the scanning picture B represents an enlarged prostate. The small ring 7 in the centre of the scanning picture represents the transducer and the resectoscope tube, whereas the bright spots around it indicate tissue interfaces.

The signal processing from the transducer to the oscilloscope is effected in a way known per se via data potentiometers and a so-called ultrasonic apparatus, which amplifies the signals and uses them for intensity modulating the cathoderay tube. The ultrasonic apparatus may be of any known kind. The electrical connection to the rotating transducer is effected by means of specially constructed slip rings which are not shown.

Further, the equipment includes a control unit transferring the representation of the rotating motion of the transducer to a rotating motion for the electron beam synchronous herewith. Said control unit includes a mechanical unit comprising a stepping motor coupled with a sine-cosine potentiometer as well as a number of electrical control circuits. The particularly important circuits are those controlling the stepping motors and the circuits which in cooperation with the sine-cosine potentiometer transfer the rotational motion of the transducer to the cathoderay tube of the oscilloscope.

What we claim is:

1. A prostate resectoscope comprising a first elongated hollow cystoscope tube having a proximal and a distal end, a pair of fixedly mounted electrically insulated conductors surrounded by said first tube and protruding from said distal end of said cystoscope tube, said protruding conductors being stripped and joined together to provide a cautery electrode, a second elongated tube of a material inert to body tissues and fluids, said second tube being surrounded by said first tube and having a proximal and a distal end, said distal end of said second tube protruding from said distal end of said cystoscope tube, a stepping motor having an output shaft secured to the proximal end of said second tube to rotate said second tube within said first tube, energizing means to supply energy to said stepping motor, and ultrasonic transducer means fixedly mounted on the distal end of said second tube and having electrical connectors passing through said second tube to transmit a beam of sound energy and to receive reflected sound energy from tissue interfaces in the prostate region to obtain, as the second tube is rotated within said first tube, an ultrasonic scanning picture in B-representation of a section of the prostate region to indicate where to make a resection in said section of the prostate region.

* * * * *